United States Patent [19]

Bartlett

[11] Patent Number: 5,782,863
[45] Date of Patent: Jul. 21, 1998

[54] APPARATUS AND METHOD FOR ANCHORING SUTURES

[76] Inventor: Edwin C. Bartlett, 609 Bremerton Dr., Greenville, N.C. 27858

[21] Appl. No.: 688,608

[22] Filed: Jul. 30, 1996

Related U.S. Application Data

[63] Continuation of Ser. No. 124,163, Sep. 20, 1993, Pat. No. 5,540,718.

[51] Int. Cl.$^6$ .................................................. A61B 17/04
[52] U.S. Cl. .................................... 606/232; 606/132
[58] Field of Search ............................. 606/232, 132, 606/72, 73, 139; 424/422

[56] References Cited

U.S. PATENT DOCUMENTS

| | | |
|---|---|---|
| 1,538,173 | 5/1925 | Daughaday . |
| 3,254,890 | 6/1966 | Watson ........................... 273/33 |
| 3,907,289 | 9/1975 | Bondu, Sr. ...................... 273/33 |
| 3,973,277 | 8/1976 | Semple et al. ....................... 3/1 |
| 4,386,971 | 6/1983 | Melton et al. ............... 148/11.5 R |
| 4,404,025 | 9/1983 | Mercier et al. ............... 148/11.5 F |
| 4,502,468 | 3/1985 | Duerig et al. ................ 148/11.5 F |
| 4,505,767 | 3/1985 | Quin ............................. 148/402 |
| 4,524,765 | 6/1985 | de Zbikowski . |
| 4,533,411 | 8/1985 | Melton .......................... 148/402 |
| 4,565,589 | 1/1986 | Harrison ........................ 148/402 |
| 4,605,414 | 8/1986 | Czajka ............................ 623/13 |
| 4,632,100 | 12/1986 | Somers et al. . |
| 4,669,473 | 6/1987 | Richards et al. . |
| 4,669,725 | 6/1987 | Taylor ............................ 273/33 |
| 4,678,470 | 7/1987 | Nashef et al. ................... 623/16 |
| 4,738,255 | 4/1988 | Goble et al. . |
| 4,741,330 | 5/1988 | Hayhurst . |
| 4,832,026 | 5/1989 | Jones . |
| 4,898,156 | 2/1990 | Gatturna et al. ................. 606/72 |
| 4,899,743 | 2/1990 | Nicholson et al. ............. 606/139 |
| 4,932,973 | 6/1990 | Gendler .......................... 623/16 |
| 4,946,468 | 8/1990 | Li ................................. 606/232 |
| 4,950,296 | 8/1990 | McIntyre ......................... 623/16 |
| 4,968,315 | 11/1990 | Gatturna .......................... 606/72 |
| 4,968,316 | 11/1990 | Hergenroeder ................... 606/90 |
| 5,002,550 | 3/1991 | Li ................................. 606/139 |
| 5,011,473 | 4/1991 | Gatturna .......................... 604/51 |
| 5,041,129 | 8/1991 | Hayhurst et al. ................ 606/232 |
| 5,046,513 | 9/1991 | Gatturna et al. ................. 128/898 |
| 5,067,962 | 11/1991 | Campbell et al. ................ 623/13 |
| 5,073,373 | 12/1991 | O'Leary et al. ................. 424/422 |

(List continued on next page.)

FOREIGN PATENT DOCUMENTS

| | | |
|---|---|---|
| 2045903 | 1/1992 | Canada . |
| 2046010 | 1/1992 | Canada . |
| 9309730 | 5/1993 | WIPO . |

OTHER PUBLICATIONS

Richmond et al., "Modification of the Bankart Reconstruction with a Suture Anchor", The American Journal of Sports Medicine, vol. 19, No. 4, pp. 343–346 (Jul./Aug. 1991).

Wolf, "Arthroscopic Capsulolabral Repair Using Suture Anchors", Orthopedic Clinics of North America, vol. 24, No. 1 pp. 59–69 (Jan. 1993).

Carpenter et al., "Pull–Out Strength of Five Suture Anchors", The Journal of Arthroscopic and Related Surgery, vol. 9, No. 1, pp. 109–113 (Feb. 1993).

*Primary Examiner*—Michael Buiz
*Assistant Examiner*—Patrick W. Rasche
*Attorney, Agent, or Firm*—Pandiscio & Pandiscio

[57] ABSTRACT

A substantially conical suture anchor having a bore in which an end of an insertion tool is inserted. The inserted end of the insertion tool is made of shape retaining material. The bore and base of the suture anchor are angled with respect to the central axis of the suture anchor and preferably are parallel to each other. During insertion, the suture anchor, mounted on the insertion tool, is reoriented to fit into the hole, thereby bending the shape memory end of the insertion tool. When the suture anchor is within cancellous bone tissue, the shape memory of the insertion tool urges the suture anchor to its original position (in which the suture anchor cannot fit through the bone hole). The suture anchor is thereby firmly anchored in the human bone.

12 Claims, 6 Drawing Sheets

U.S. PATENT DOCUMENTS

| | | | |
|---|---|---|---|
| 5,100,417 | 3/1992 | Cerier et al. | 606/139 |
| 5,102,421 | 4/1992 | Anspach, Jr. | 606/232 |
| 5,112,354 | 5/1992 | Sires | 623/16 |
| 5,141,520 | 8/1992 | Goble et al. | 606/232 |
| 5,156,616 | 10/1992 | Meadows et al. | 606/232 |
| 5,174,087 | 12/1992 | Bruno | 53/430 |
| 5,176,682 | 1/1993 | Chow | 606/72 |
| 5,179,915 | 1/1993 | Cohen et al. | 606/62 |
| 5,192,303 | 3/1993 | Gatturna et al. | 606/232 |
| 5,203,787 | 4/1993 | Noblitt et al. | 606/232 |
| 5,207,679 | 5/1993 | Li | 606/72 |
| 5,211,647 | 5/1993 | Schmieding | 606/104 |
| 5,217,486 | 6/1993 | Rice et al. | 606/232 |
| 5,258,016 | 11/1993 | DiPoto et al. | 606/232 |
| 5,269,809 | 12/1993 | Hayhurst et al. | 606/232 |
| 5,290,558 | 3/1994 | O'Leary et al. | 424/422 |
| 5,298,254 | 3/1994 | Prewett et al. | 424/422 |
| 5,312,438 | 5/1994 | Johnson | 606/232 |
| 5,423,860 | 6/1995 | Lizardi et al. | 606/232 |
| 5,439,684 | 8/1995 | Prewett et al. | 424/422 |
| 5,492,697 | 2/1996 | Boyan et al. | 424/422 |
| 5,540,718 | 7/1996 | Bartlett | 606/232 |

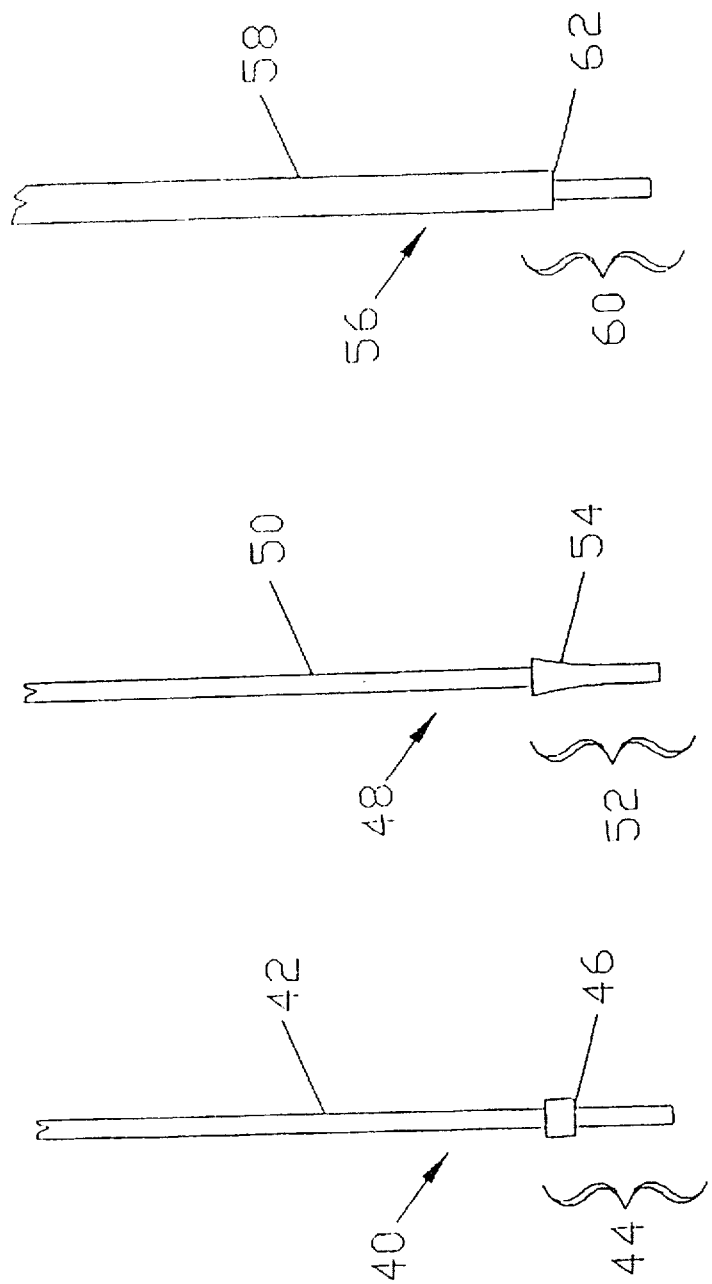

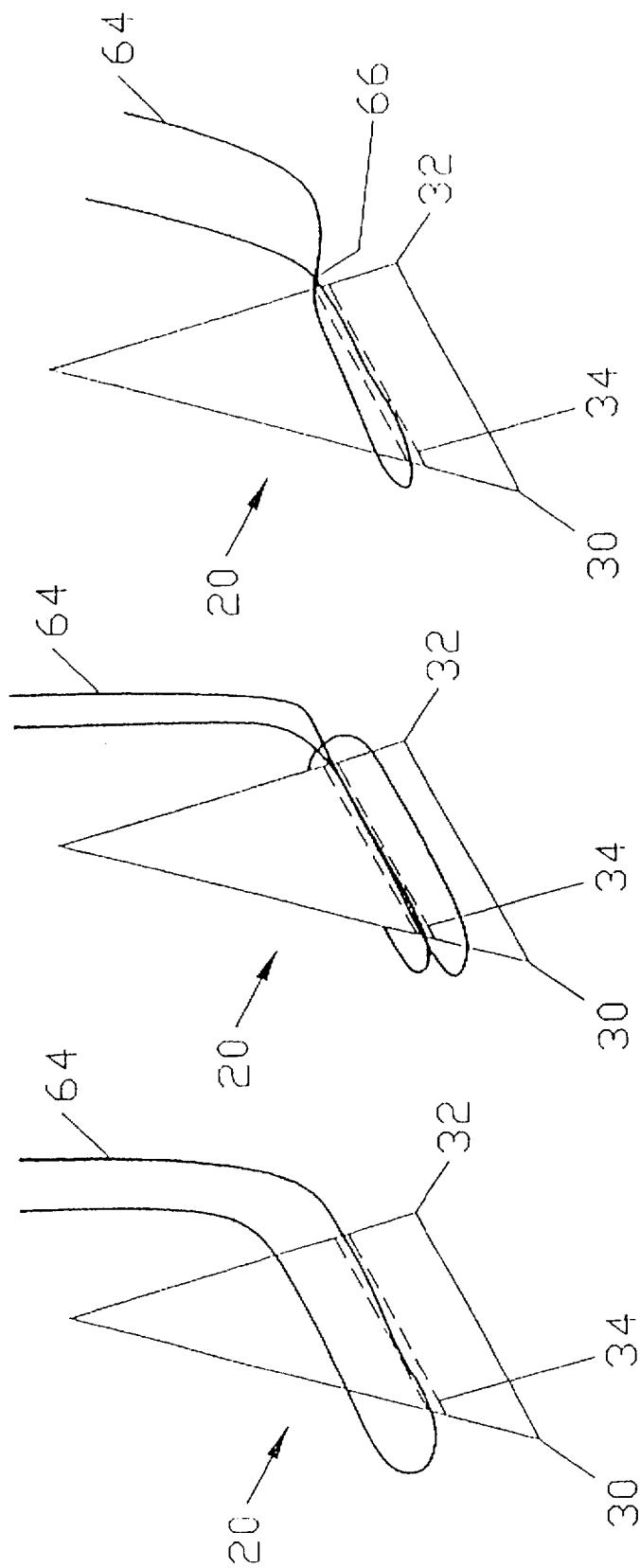

APPARATUS AND METHOD FOR ANCHORING SUTURES

This application is a con. of Ser. No. 08/124,163 filed Sep. 20, 1993, now U.S. Pat. No. 5,540,718.

BACKGROUND OF THE INVENTION

This invention relates to an apparatus and method for anchoring sutures to a live human bone. More particularly, this invention relates to a suture anchor made of a substantially rigid, preferably biocompatible material, and most preferably a material that can be incorporated into the bone as a bone graft, such as bone, and an insertion tool having a portion made of a stress-induced shape memory material which is inserted into the anchor and functions to orient the suture anchor, once inserted in the bone, to securely anchor the suture.

Suture anchors for anchoring a suture to bone so that another body tissue, such as muscle or ligament, may be sutured to the bone are known in the art. Such suture anchors come in a variety of shapes and designs. A survey of such suture anchors may be found in James E. Carpenter et al., "Pull-Out Strength of Five Suture Anchors", *Arthroscopy*, 9(1), pp. 109–113 (1993).

For example, harpoon-type or screw-type suture anchors are drilled into cortical bone. Examples of such suture anchors are shown, for example, in Cerrier et al. U.S. Pat. No. 5,100,417 and Hayhurst et al. Canada Patent No. 2,045,903. Such suture anchors are held in place in any of a variety of manners, such as through self-tapping, by a force fit, or by including a resilient portion which flexes to frictionally engage the bone material.

Another type of suture anchor includes a rigid member and a resilient, shape memory member. The resilient member is substantially flush with the rigid member during insertion, and flexes away from the rigid member once lodged inside the bone. Such anchors have been described in Gatturna et al. U.S. Pat. Nos. 5,046,513 and 5,192,303. The shape memory material may be made in accordance with, for example, Quin U.S. Pat. No. 4,505,767 or Harrison U.S. Pat. No. 4,565,589. Because two different materials are used, this type of suture anchor can be costly and difficult to manufacture. Moreover, the joining of two dissimilar metals leads to potential flaws and potential breakage at the joint or weld point.

A third type of suture anchor is substantially elongated and is inserted with its longitudinal axis substantially parallel to the bone hole through which it is inserted. The suture anchor is then reoriented upon reaching cancellous bone tissue by pulling on the suture attached at a selected point along the suture anchor. Examples of such suture anchors are shown in Hayhurst et al. U.S. Pat. No. 5,041,129 ("Hayhurst") and Noblitt et al. U.S. Pat. No. 5,203,787 ("Noblitt"). The Hayhurst suture anchor has a substantially cylindrical rigid body with a central bore and a longitudinal slot extending from one end to approximately the middle of the rigid body. A suture is positioned inside the central bore, and the anchor is inserted with the slot entering the bone last. Once the anchor is properly positioned, the suture is pulled through the slot towards the base of the slot, thereby reorienting the suture anchor to fix the anchor in the bone. The Noblitt suture anchor has an offset portion at which a suture is attached. Once the suture anchor is within cancellous tissue, the suture is pulled, thereby reorienting the suture anchor so that its longitudinal axis is substantially transverse to the bone hole through which it was inserted.

One disadvantage associated with this type of anchor is that tugging on the suture to reorient the anchor may put undue stress on the suture (particularly at the base of the slot in Hayhurst). Moreover, the introduction technique is unduly complicated, requiring several types of insertion tools (Noblitt may provide additional complications because of the nonuniform thickness of the suture anchor along the longitudinal axis). Furthermore, Hayhurst's slot may structurally weaken the remainder of the suture anchor body, and Noblitt's elongated, narrow ends may tend to break off during reorientation.

A disadvantage common to all of the above-described suture anchors is that many are typically formed of metal which may not be biocompatible. Additionally such suture anchors are typically visible during X-ray, magnetic resonance imaging (MRI), and computerized tomography (CT) examinations. Accordingly, these suture anchors may interfere with noninvasive examinations of the treated area. Moreover, the above-described suture anchors typically require complex insertion tools, the use of which is time consuming. There is thus greater potential for later complications such as bone weakening.

Two other anchoring means are staples and cement. The former is generally not desirable because staples can crack the bone in which they are inserted or damage the tissue to be connected to the bone. The latter is generally not desirable because of substance compatibility, the need for particular surface characteristics for adequate bonding, and excessive setting times.

It therefore would be desirable to provide an apparatus for anchoring a suture to a bone which is simple to manufacture and to insert, which does not interfere with noninvasive examinations such as radiographs, MRI, or CT, and which is biocompatible and most preferably, capable of being incorporated into the bone as a bone graft, to strengthen the bone. Alternatively, the apparatus may be bioabsorbable.

It would also be desirable to provide a method and apparatus for inserting a suture anchor which results in a minimal number of insertion steps and requires a minimal number of tools.

SUMMARY OF THE INVENTION

It is an object of this invention to provide a suture anchor which is simple and inexpensive to manufacture and easy to insert, as well as a method of insertion which is relatively straightforward having a minimal number of steps, requiring a minimal number of insertion tools. Such a suture anchor reduces later complications such as bone weakening.

It is also an object of this invention to provide a suture anchor which does not interfere with noninvasive examinations such as by radiographs, MRI, or CT, and is biocompatible, thus potentially causing bone strengthening after implantation. Alternatively, the suture anchor may be formed from a bioabsorbable material.

These and other objects of the invention are accomplished in accordance with the principles of this invention by providing a substantially rigid suture anchor, preferably made of bone, which is reoriented after insertion to be securely positioned inside a bone. A single insertion tool pushes the suture anchor through a previously drilled hole in the bone. The insertion tool includes at least a portion made of shape memory material which is deformed during insertion of the suture anchor but which returns to its initial configuration when the suture anchor is free to rotate (e.g., when in cancellous bone tissue), thereby reorienting the suture anchor to be securely positioned in the bone.

BRIEF DESCRIPTION OF THE DRAWINGS

The above and other objects and advantages of the invention, its nature, and various features will be more apparent from the following detailed description of the preferred embodiments, taken in conjunction with the accompanying drawings (in which like reference characters represent like elements throughout), and in which:

FIG. 3 is a side view of an insertion tool in accordance with the principles of this invention;

FIG. 4 is a side view of an alternative embodiment of an insertion tool in accordance with the principles of this invention;

FIG. 5 is a side view of another alternative embodiment of an insertion tool in accordance with the principles of this invention;

FIG. 6 is a side view of a suture joined to the suture anchor of the present invention;

FIG. 7 is a side view of an alternative manner of joining a suture to the suture anchor of the present invention; and FIG. 8 is a side view of another alternative manner of joining a suture to the suture anchor of the present invention.

DETAILED DESCRIPTION OF THE INVENTION

Figure 2:
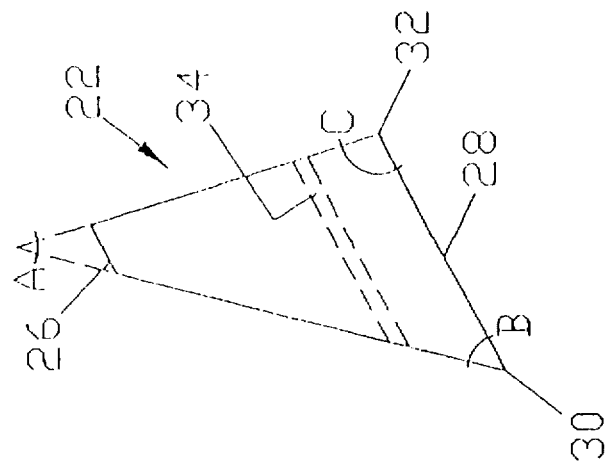
FIG. 2 is a side view of a modified suture anchor in accordance with the principles of this invention.
Figure 1:
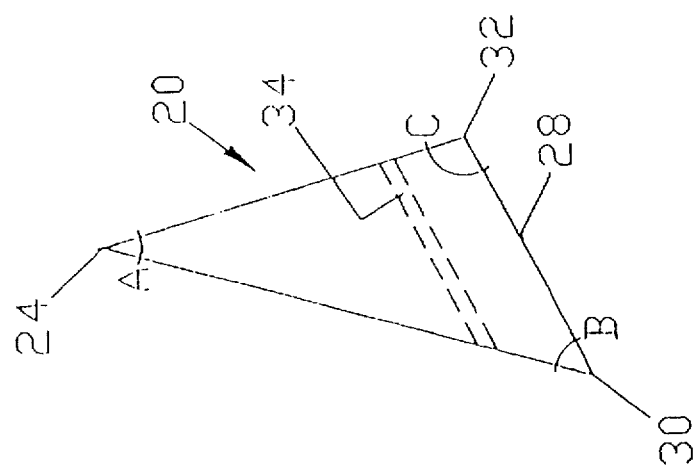
FIG. 1 is a side view of a suture anchor in accordance with the principles of this invention.

A suture anchor constructed in accordance with the principles of the present invention is shown in FIGS. 1 and 2. Suture anchors 20 and 22 are formed from a material which is biocompatible. Preferably, the selected material strengthens the bone in which the anchor is inserted. Additionally, it is desirable for the selected material to be transparent to noninvasive examinations such as by radiograph (e.g., X-ray). Accordingly, the most preferred material for the suture anchors of the present invention is cortical bone. The suture anchor of the present invention is preferably formed from strips of cortical bone cut from the midshaft of a human femur. Autologous bone can be used, but can be difficult to obtain. Allogeneic cortical bone is the preferred material, however, the use of xenogeneic cortical bone tissue is also contemplated. The suture anchor of the present invention may also be formed of a suitable biocompatible polymer or biocompatible metal or other biocompatible material. Such metals and materials should preferably be FDA approved for use in humans. Alternatively, one of a variety of known bioabsorbable materials may be used.

Although the method of insertion of the present invention may utilize a suture anchor of any desirable elongated shape, such as a cylinder, the suture anchor of the present invention is preferably substantially conical, i.e., either a complete cone or a truncated cone (e.g., a frustum). As shown in FIG. 1, suture anchor 20 is completely conical, having an apex 24. A conical suture anchor may easily be formed by inserting an end of a strip of the desired material into a milling device. Such milling devices are well known in the art—and may be designed for milling bone or other materials in accordance with the principles of a common pencil sharpener. Apex 24, or a portion thereof, is useful for cutting through cancellous bone tissue once suture anchor 20 passes through the cortical bone tissue. For greater strength in the apical area, it may be desirable to cut off the apex of the conical suture anchor to form a flattened trailing end 26, resulting in a frustoconical suture anchor 22, such as shown in FIG. 2. The amount by which the cone apex is truncated should preferably maximize the structural strength of the apical region of the suture anchor, while retaining a general conical shape. This enables travel through cancellous bone tissue during reorientation of the suture anchor. It should be appreciated that the optimum shape of the suture anchor may vary according to the site of use in the patient. One of ordinary skill in the art could determine, by routine experimentation, the optimum shape of the suture anchor for a particular application at a particular site of use. Both suture anchor 20 and suture anchor 22 preferably have generally circular conical surfaces (thereby facilitating manufacture) and each has a base 28 which preferably is cut oblique to the central axis of the cone. The angle at which base 28 is cut is discussed in more detail below.

Angle A of apex 24 is selected to efficiently cut through cancellous bone tissue and can range from 10°–60°. Preferably, apex angle A is between 20°–40°. The exact angle will depend on the milling apparatus used, and most typically is approximately 20°. Apex angle A generally is determined first, setting the range of possible lengths for the suture anchor. The length of suture anchor 20 or 22 is selected to provide the strongest suture anchor which can fit through the patient bone hole in which the suture anchor is to be positioned, and which can accommodate the suture required for the particular operation. The size of the patient bone hole through which the suture anchor is inserted is within the range of 1–12 mm, typically within 2–6 mm. Preferably, the patient bone hole is within 2.5–3.5 mm. The patient bone hole is formed according to any desired method, utilizing any suitable means.

Because base 28 of suture anchors 20 and 22 is cut oblique to the central axis, the angle formed between the conical surface and the base of suture anchors 20 and 22 varies along the circumference of base 28. The leading bottom edge 30 (the first area of the edge of base 28 to enter the patient bone hole through which the suture anchor is to be positioned) preferably has the smallest angle B between the conical surface and base 28. Trailing edge 32, opposite leading bottom edge 30, is at angle C, the largest angle between the conical surface and base 28. The specific angle at which base 28 is cut with respect to the suture anchor's central axis is determined primarily by the size of the patient bone hole, to achieve the most easily insertable suture anchor. The measurement of apex angle A and the desired length of the suture anchor also affect the angle at which base 28 should be cut. Typically, if the suture anchor is to be inserted with base 28 parallel to the walls of the patient bone hole (as described in more detail below), base 28 should be cut such that the distance from trailing edge 32, when measured perpendicular to base 28, to the conical surface joining leading edge 30 and apex 24 is no greater than the width of the patient bone hole. In other words, when the suture anchor is inserted into the patient bone hole (with base 28 parallel to the walls of the patient bone hole) trailing edge 32 should be able to fit into the patient bone hole as well in order to ensure that the remainder of the suture anchor will be able to fit through the patient bone hole. Preferably, this distance is approximately 0.2–0.5 mm less than the patient bone hole. Typically, the resulting angle C is between 90°–165°.

Both suture anchors 20 and 22 have an anchor bore 34 in which the insertion tool is positioned to insert the suture anchor, and also through which the suture generally is threaded. Accordingly, the diameter of bore 34 is determined by the diameters of the insertion tool to be used and the suture to be anchored, and typically is between 1/32–1/16 inches. Bore 34 need not be cylindrical, and may have any of a variety of cross-sectional shapes. Preferably, the shape of bore 34 includes a section in which the suture can travel to minimize contact between the suture and the insertion tool during the insertion process. Potential cross-sectional shapes for bore 34 thus include oblong, elliptical, tear-drop, a figure eight (thereby providing separate bores for the suture and the insertion tool), substantially circular with a slot for the suture to run through, or any other shape that can accommodate the suture as described. The entry and exit areas of bore 34 preferably are chamfered to reduce stress on the suture when the suture is pulled during suturing. Bore 34 is preferably cut at an angle oblique to the axis of the suture anchor. Preferably, bore 34 and base 28, and flattened trailing end 26 (when present) are parallel. However, it is within the scope of the present invention to form bore 34, base 28, and flattened trailing end 26 at different angles with respect to the axis of the suture anchor.

In order to function properly, the insertion tool should be limited in travel through bore 34 of the suture anchor. Accordingly, the insertion tool of the present invention has a means for limiting the travel of its insertion end into bore 34. Examples of insertion tools having means for limiting insertion end travel are shown in FIGS. 3–5.

Insertion tool 40 of FIG. 3 has a substantially straight elongated body 42 ending with insertion end 44, which is inserted inside bore 34 of the suture anchor. Bead 46 demarcates insertion end 44 from the remainder of body 42 and prevents body 42 from entering bore 34. The diameter of insertion end 44 should be sufficiently wide to provide a close fit inside bore 34 of the suture anchor (also accounting for the amount of suture material positioned inside bore 34). The diameter of bead 46 should be substantially larger in diameter than bore 34 in order to limit movement of insertion end 44 through bore 34.

Insertion tool 48 of FIG. 4 has a substantially straight elongated body 50, similar to body 42. However, insertion end 52 is wedged, with the narrowest part at the free end of insertion tool 48. The dimensions of wedge 54 are selected to securely fit within bore 34 of the suture anchor (with the suture also threaded through bore 34) to hold the suture anchor during insertion into the patient bone. It will be appreciated that one or both sides of insertion tool 48 may be wedged.

Insertion tool 56 of FIG. 5 has a substantially straight elongated body 58. Insertion end 60 is narrower than body 58 and distinctly begins at step 62. Insertion end 60 must be sufficiently thick to form a tight fit within bore 34 of the suture anchor (with the suture also threaded through bore 34) during insertion into the patient bone hole. Again, it will be appreciated that one or both sides of insertion tool 56 may be stepped.

For reasons as will be described in connection with the method of insertion, at least insertion ends 44, 52, and 60 of insertion tools 40, 48, and 56, respectively, should be formed from a shape memory material. The memory should be retained such that the insertion end is not permanently deformed during insertion of the suture anchor and will return the insertion end to an initial configuration (generally the configuration of the insertion end at the time it is initially mounted in bore 34, prior to insertion of the suture anchor into the patient bone). The preferred material for at least the insertion end of the insertion tool is a nickel titanium alloy. Such materials are available commercially, under the names "NITINOL" or "TINEL" (RayChem) or "SENTINOL" (GAC International, Inc.). Such shape memory alloys are well known in the art. See, e.g., U.S. Pat. Nos. 4,505,767, and 4,565,589. However, any other shape retaining material sufficient for properly inserting the suture anchor of the present invention into a patient bone hole may be used.

Any suitable means for attaching the suture to the suture anchor may be used within the scope of the invention. Suture 64 may be threaded through bore 34 of the suture anchor in any preferred manner, such as those illustrated in FIGS. 6–8. In FIG. 6, one end of suture 64 is threaded through bore 34 and looped around the conical surface of suture anchor 20 adjacent leading edge 30. Thus, suture 64 passes through suture anchor 20 only once, as thread through the eye of a needle. When threaded in this manner, suture 64 can freely travel through bore 34. Adjustment of the position of suture 64 through bore 34 by pulling one of the free ends of suture 64 may cause the suture anchor to rotate approximately 90°.

Suture 64 may, instead, be more fixedly threaded through bore 34, as shown in FIGS. 7 and 8. In FIG. 7, suture 64 is looped over suture anchor 20, and the free ends of suture 64 are then threaded through the end of bore 34 adjacent leading edge 30, exiting bore 34 adjacent trailing edge 32. Suture 64 is then pulled to tighten the loop around suture anchor 20. When an end of suture 64 is pulled, suture anchor 20 will barely rotate, if at all, maintaining bore 34 relatively parallel to the patient bone hole.

Suture 64 is knotted to anchor 20 in FIG. 8. As shown in FIG. 8, only one end of suture 64 is threaded through bore 34 as in FIG. 6. However, upon exiting bore 34, knot 66 is formed with the ends suture 64 at the exit of bore 34, preferably adjacent trailing edge 32. As in FIG. 7, the manner of threading shown in FIG. 8 may produce minimal rotation of suture anchor 20 if an end of suture 64 is pulled.

The preferred method of inserting the suture anchor of the present invention is illustrated in FIGS. 9–16. A patient bone hole 70 has already been drilled into patient bone 72. Patient bone hole 70 extends completely through cortical bone matter 74. Patient bone hole 70 may also extend, at least partially, through cancellous bone tissue 76, preferably to a depth about equal to the length of the suture anchor. It will be understood that any insertion tool with a shape memory insertion end may be used in the preferred insertion method. Moreover, any suitable substantially rigid anchor with a bore for the insertion tool may be used.

Figure 9:
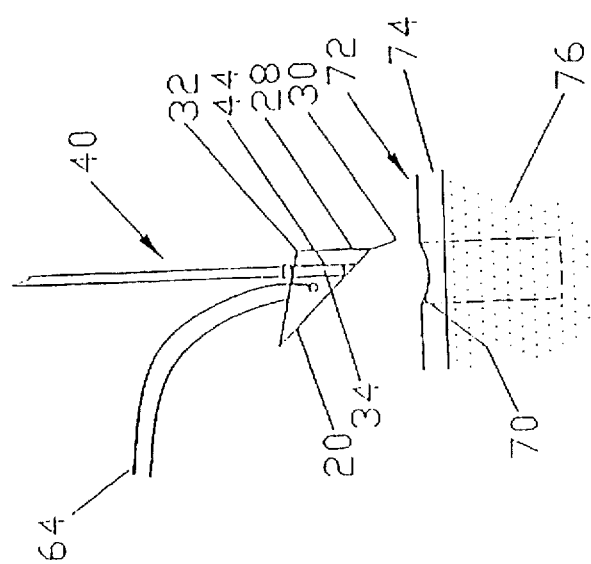
FIG. 9 is a side view of a suture anchor mounted on an insertion tool and carrying a suture, in preparation for insertion into a bone.

As shown in FIG. 9, suture anchor 20 is mounted on insertion end 44 of insertion tool 40, and suture 64 is threaded through bore 34. Insertion end 44 enters bore 34 adjacent trailing edge 32 of suture anchor 20 and exits (if at all) adjacent leading edge 30. Because insertion end 44 of tool 40 is securely positioned within bore 34, bore 34 is not easily distinguishable, in the FIGS., from the outer surface of insertion end 44. Bore 34 is preferably drilled parallel to base 28. Insertion tool 40 is positioned parallel to the axis of patient bone hole 70, maintaining bore 34 and base 28 (if bore 34 is drilled parallel to base 28) parallel to patient bone hole 70, as well. Leading edge 30 of suture anchor 20 is positioned to be the first portion of suture anchor 20 to enter patient bone hole 70.

Figure 10:
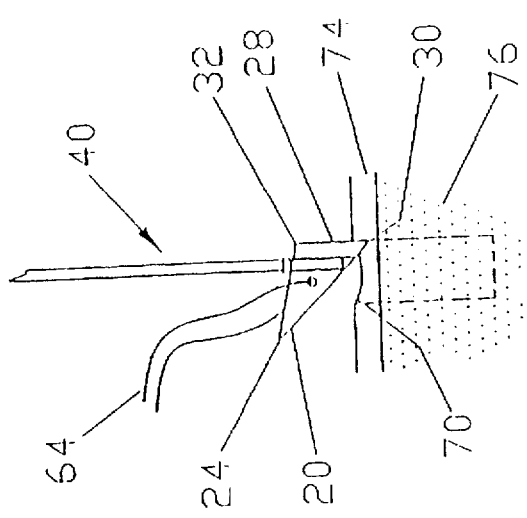
FIG. 10 is a side view of a suture anchor mounted on an insertion tool and in the initial stages of insertion into a bone.

Initial entry of suture anchor 20 into patient bone hole 70 is shown in FIG. 10. The conical surface extending between leading edge 30 and apex 24 has not yet encountered patient bone hole 70. As alluded to above, this portion of the conical surface of suture anchor 20 should not encounter patient bone hole 70 until trailing edge 32 also encounters patient bone hole 70.

Figure 11:
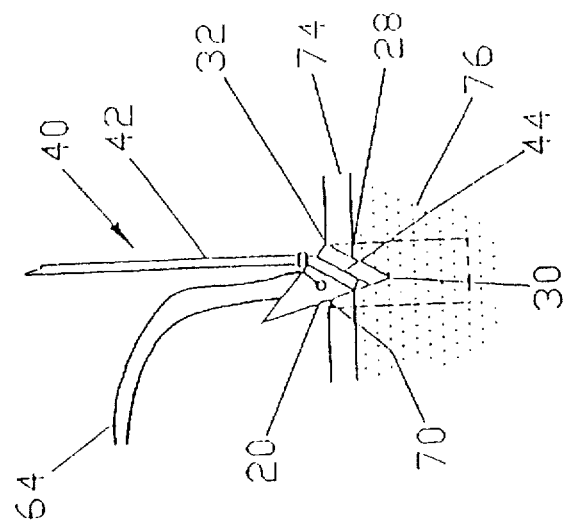
FIG. 11 is a side view of a suture anchor mounted on an insertion tool, shown once insertion into a bone has begun.

Once the conical surface extending between leading edge 30 and apex 24 encounters patient bone hole 70, suture anchor 20 begins to rotate or reorient, as shown in FIG. 11, in order to fit into patient bone hole 70. Main body 42 of insertion tool 40 is maintained parallel to patient bone hole 70. Thus, when suture anchor 20 reorients, insertion end 44 bends.

Figure 14:
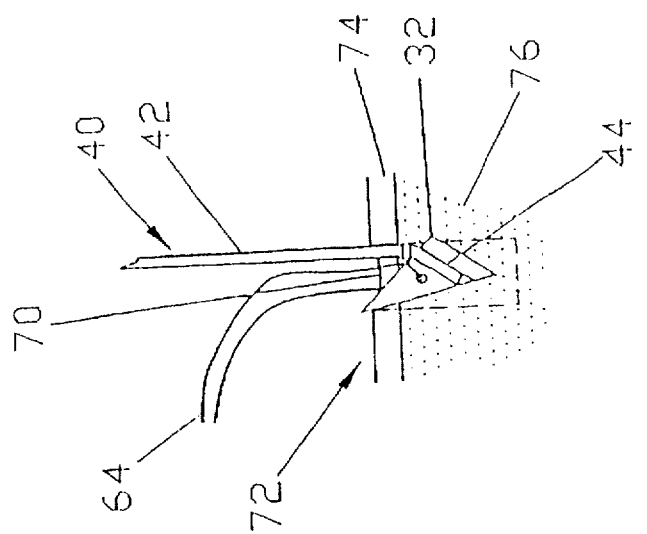
FIG. 14 is a view similar to that of FIG. 13, but shows the suture anchor almost completely inside the bone, but not yet within anchoring position.
Figure 13:
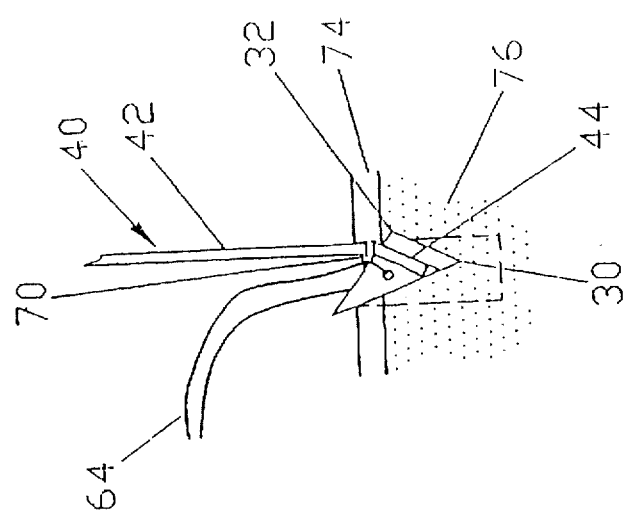
FIG. 13 is a view similar to that of FIG. 12, but shows the insertion tool beginning to resume its initial configuration.
Figure 12:
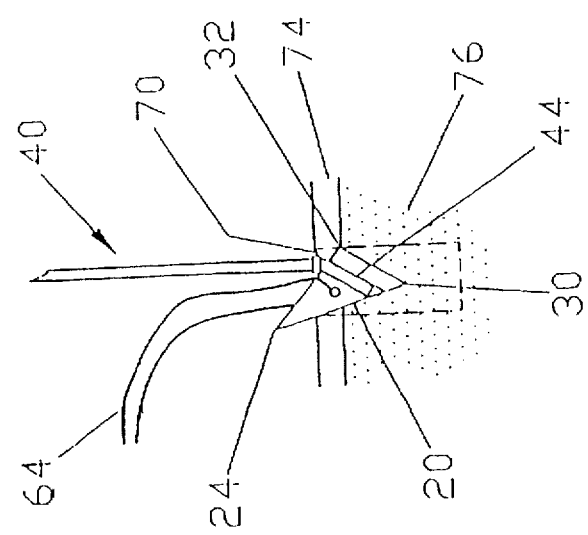
FIG. 12 is a view similar to that of FIG. 11, but shows further progress of the suture anchor and insertion tool into the bone, in the position at which the insertion tool is in its most deformed state.

Typically, insertion end 44 is bent to the greatest extent immediately before trailing edge 32 leaves the portion of patient bone hole 70 in patient cortical bone tissue 74, as shown in FIG. 12. Once trailing edge 32 begins travelling through patient cancellous bone tissue 76, insertion end 44 begins to resume its initially straight configuration, as shown in FIGS. 13 and 14. Preferably main body 42 of insertion tool 40 is not as flexible as insertion end 44, and remains straight throughout the insertion procedure. As best seen in FIG. 14, as suture anchor 20 travels deeper into patient bone 72, right trailing edge 32 travels further, and the greater influence the insertion tool's shape memory has over the configuration of insertion end 44.

Figure 16:
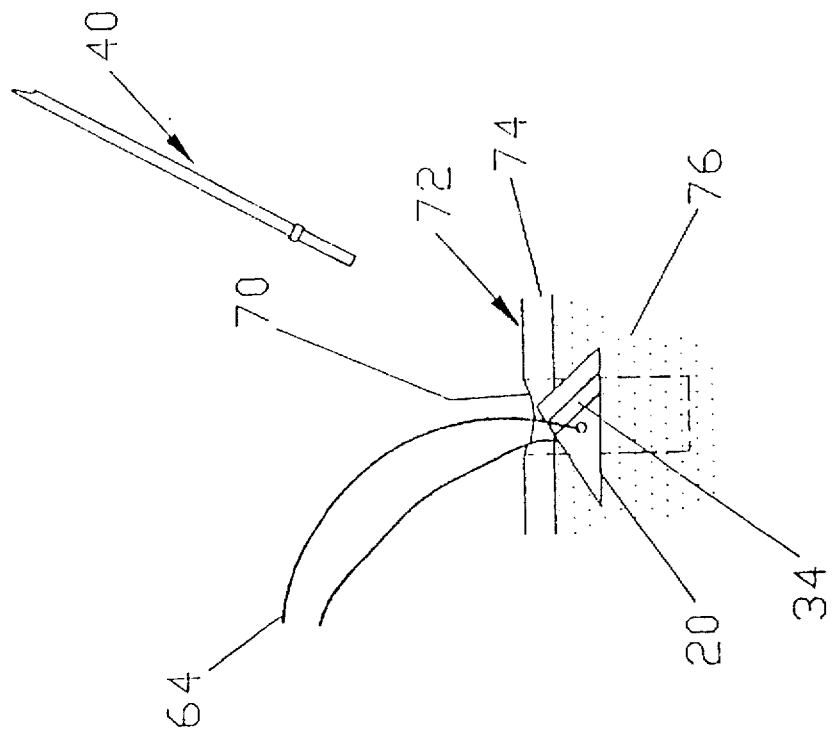
FIG. 16 is a side view of a suture anchor in a final anchoring position, dismounted from the insertion tool.
Figure 15:
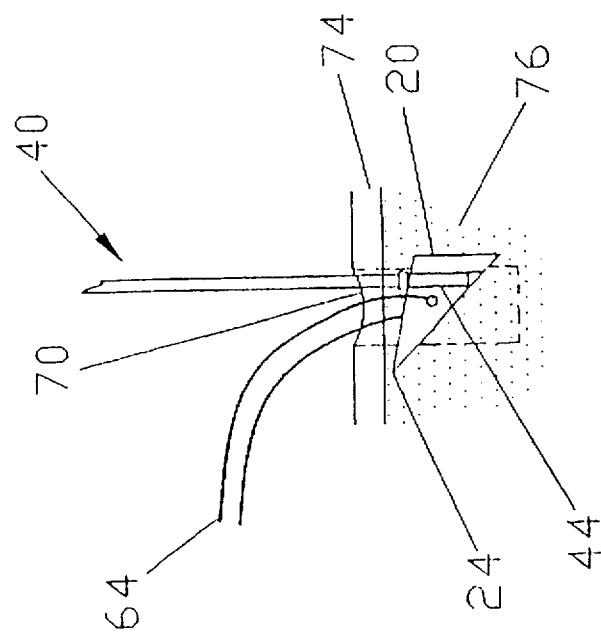
FIG. 15 is a side view of a suture anchor completely positioned in cancellous bone tissue, the suture anchor still mounted on the insertion tool, which has resumed its initial configuration.

Once apex 24 has cleared patient cortical bone tissue 74, and the entire suture anchor is in cancellous bone tissue 76, insertion end 44 of insertion tool 40 is free to return to its original configuration, as shown in FIG. 15. The pointed apex 24 allows suture anchor 20 to travel counterclockwise, easily cutting through cancellous bone tissue 76. As shown in FIG. 16, insertion tool 40 can then be removed. Preferably suture 64 is pulled up and away from patient bone 72 to firmly position suture anchor 20 in patient bone 72, preferably against the undersurface of cortical bone 74, within the transition region between cortical bone matter 74 and cancellous bone matter 76. Typically, suture 64 will be substantially centered within patient bone hole 70, and suture anchor 20 will be substantially horizontal. Suturing of body tissue to patient bone 72 can now be commenced.

It will be understood that the foregoing is merely illustrative of the principles of this invention, and that various modifications can be made by those skilled in the art without departing from the scope and spirit of the invention. For example, the suture anchors and insertion tools used in the preferred insertion method (illustrated in FIGS. 9–16) may be formed in shapes other than those illustrated, but which will function in accordance with the method of the present invention. Moreover, it will be appreciated that although it is not necessary to use the insertion tools typically used during suture anchor insertion (such as cannulas), the use of such tools is contemplated within the scope of the present invention.

While we have hereinbefore described a number of embodiments of this invention, it is apparent that our basic embodiments can be altered to provide other embodiments that utilize the inventive concepts of this invention. Therefore, it will be appreciated that the scope of this invention includes all alternative embodiments and variations which are defined in the foregoing specification and by the claims appended hereto; and the invention is not to be limited by the specific embodiments that have been presented herein by way of example.

What is claimed is:

1. A suture anchor for disposition in a patient bone hole of a selected diameter, the suture anchor comprising:

a rigid body having a leading edge, a biting edge, a base wall interconnecting said leading edge and said biting edge, a trailing edge, a first wall portion interconnecting said leading edge and said trailing edge, a second wall portion interconnecting said biting edge and said trailing edge;

a distance from said first wall portion to said biting edge, taken perpendicularly to said first wall portion, exceeding the patient bone hole diameter;

said body defining a bore extending from said base wall to said second wall portion for receiving and retaining a suture and an inserter tool distal end, said bore being spaced from said first wall portion by less than half of said distance;

wherein upon introduction of said base wall to the patient bone hole, said leading edge and said first wall portion enter the hole and said base wall, proximate said biting edge, engages a bone surface adjacent the hole, causing said body to pivot in the hole such that said leading edge, said first wall portion, and said base wall enter the hole, followed by said biting edge, said second wall portion, and said trailing edge; and wherein upon movement of said body in the hole, said biting edge bites into a side wall of the hole to lock the anchor in the hole.

2. The suture anchor of claim 1, wherein said bore is parallel to a plane of said base wall.

3. The suture anchor according to claim 1, said suture anchor consisting of milled bone.

4. The suture anchor of claim 3, wherein said milled human bone is milled human cortical bone.

5. A system for anchoring a suture to live human bone in a substantially cylindrical bone hole of a selected diameter and having a longitudinal axis, said system comprising:

a suture anchor including a rigid body having a leading edge, a biting edge, a base wall interconnecting said leading edge and said biting edge, a trailing edge, a first wall portion interconnecting said leading edge and said trailing edge, a second wall portion interconnecting said biting edge and said trailing edge, a distance from said first wall portion to said biting edge, taken perpendicularly to said first wall portion, exceeding the bone hole diameter, the body defining a bore extending from said base wall to said second wall portion for receiving and retaining a suture, the bore being spaced from said first wall portion by less than half of said distance; and an insertion tool having a resilient distal end portion received by said bore in said body, said tool distal end portion being bendable but biased to return to its original configuration and disposition, and a rigid portion connected to said distal end portion;

wherein upon lodgment of said tool distal end in said anchor bore and upon advancing of said anchor base wall to said bone hole, said leading edge and said first wall portion enter the hole and said base wall, proximate said biting edge, engages a bone surface adjacent the hole, causing said anchor to pivot in the hole such that said leading edge, said first wall portion, and said base wall portion enter the hole, said pivoting movement of said anchor being permitted by said tool resilient distal end, and wherein upon continued advancement of said tool into the hole along the axis of the hole, said biting edge, said trailing edge, and said second wall portion enter the hole;

whereupon said distal end of said tool moves toward return to its original configuration and disposition to move said anchor in the hole, to cause said biting edge to bite into a side wall of the hole to lock said anchor in the hole.

6. The system of claim 5, wherein said suture anchor has a conical surface, a base wall, and a central axis.

7. The system of claim 6, wherein:

the angle of said base wall with respect to said central axis of said suture anchor is oblique; and said conical surface is a circular conical surface.

8. The system of claim 5, wherein said insertion tool further includes means for limiting the movement of said insertion tool distal end portion into said bore.

9. A method for anchoring a suture to live human bone in a substantially cylindrical bone hole having a longitudinal axis and a diameter, the method comprising the steps of:

providing a suture anchor including a rigid body having a leading edge, a biting edge, a base wall interconnecting said leading edge and said biting edge, a trailing edge, a first wall portion interconnecting said leading edge and said trailing edge, a second wall portion interconnecting said biting edge and said trailing edge, a distance from said first wall portion to said biting edge, taken perpendicularly to said first wall portion, exceeding the bone hole diameter, the body defining a bore extending from said base wall to said second wall portion for receiving and retaining a suture, the bore being spaced from said first wall portion by less than half of said distance;

providing an insertion tool having a resilient distal end portion received by said bore in said body, said tool distal end portion being bendable but biased to return to its original configuration and disposition, and a rigid portion connected to said distal end portion;

threading a suture through said anchor bore;

mounting said anchor on said tool distal end by inserting said tool distal end in said bore;

advancing said anchor base wall to the hole by advancing said tool along the hole longitudinal axis, such that said leading edge and said first wall portion enter the hole and said base wall, proximate said biting edge, engages a bone surface adjacent the hole, causing said anchor to pivot in the hole such that said leading edge, said first wall portion, and said base wall portion enter the hole, the pivoting movement of the anchor being permitted by the tool resilient distal end; and further advancing said tool into the hole along the axis of the hole, such that said biting edge, said trailing edge and said second wall portion enter the hole;

whereupon said distal end of said tool moves toward return to its original configuration and disposition to move said anchor in the hole, to cause said biting edge to bite into a side wall of the hole to lock the anchor in the hole.

10. The method of claim 9, further including the step of pulling said suture away from said bone hole after said suture anchor has been reoriented inside said bone hole, to thereby further secure said suture anchor in said bone hole.

11. A method of forming a suture anchor for inserting into live human bone to secure an end of a suture to said live human bone, said method comprising the steps of:

cutting a bone into strips;

milling one of said strips of said bone to form an elongated shape having a longitudinal axis; and drilling a bore in said milled strip of bone at a first angle to said longitudinal axis, wherein said milling step includes the step of milling said strip of bone to form a substantially conical solid having a conical surface and a base, and said longitudinal axis comprises a central axis.

12. The method of claim 11, wherein:

said drilling step includes drilling said bore oblique to said central axis; and said method further comprises the step of cutting said base substantially parallel to said bore.

* * * * *